United States Patent [19]

Mitchell et al.

[11] Patent Number: 4,694,070

[45] Date of Patent: Sep. 15, 1987

[54] WATER SOLUBLE XANTHYLIUM DERIVATIVES SUBSTRATES

[75] Inventors: Gary A. Mitchell, Miami Lakes; Gerald E. Jaffe, Pembroke Pines; Marilyn M. Solorzano, Sunrise, all of Fla.

[73] Assignee: Coulter Electronics, Inc., Hialeah, Fla.

[21] Appl. No.: 737,761

[22] Filed: May 28, 1985

[51] Int. Cl.$^4$ ............................ C07K 7/06; C12Q 1/38
[52] U.S. Cl. ..................................... 530/329; 530/802; 435/23
[58] Field of Search ....................... 530/331, 329, 802; 435/23

[56] References Cited

U.S. PATENT DOCUMENTS

| | | | |
|---|---|---|---|
| 4,275,153 | 6/1981 | Gargiulo et al. | 435/13 |
| 4,279,810 | 7/1981 | Claeson et al. | 435/23 |
| 4,294,923 | 10/1981 | Smith et al. | 435/23 |
| 4,336,186 | 6/1982 | Gargiulo et al. | 435/23 |
| 4,557,862 | 12/1985 | Mangel et al. | 530/331 |

OTHER PUBLICATIONS

Leytus et al., Rhodamine-Based Compounds as Fluorogenic Substrates for Serine Proteinases, Biochem. Journal, (1983), 209, pp. 299-307.

Leytus et al., New Class of Sensitive and Selective Fluorogenic Substrates for Serine Proteinases, Biochem. Journal, (1983), 215, pp. 253-260.

Batsakis and Savory (editors), Critical Reviews in Clinical Laboratory Sciences, (1981), pp. 25-84.

Duncan et al., A Clinical Evaluation of Automated Chromogenic Tests as Substitutes for Conventional Prothrombin Time and Activated Partial Thromboplastin Time Tests, Clin. Chem., vol. 31, No. 6, (1985), pp. 853-855.

*Primary Examiner*—Delbert K. Phillips
*Attorney, Agent, or Firm*—Gerald R. Hibnick

[57] ABSTRACT

Water soluble xanthylium derivative substrates of rhodamine 110 and rhodol permit spectrophotometric and fluorescent measurements of trypsin-like enzymes without the addition of organic solvent additives and/or special water solubilizing agents. These novel substrates exhibit increased sensitivity for determining low levels of activity of trypsin-like enzymes such as proteolytic enzymes, cofactors, activators, antiactivators, and inhibitors. These substrates can be substituted for fibrinogen or monitor the pathways of blood coagulation.

4 Claims, No Drawings

WATER SOLUBLE XANTHYLIUM DERIVATIVES SUBSTRATES

FIELD OF THE INVENTION

This invention relates to water soluble xanthylium derivative substrates, method of their synthesis, and utilization of such synthetic substrates for measurement of the activity of protease enzymes, inhibitors, cofactors, activators, and antiactivators, individually or in combination with each other.

BACKGROUND OF THE INVENTION

Synthetic rhodamine 110 derivative substrates heretofore have Oeen utilized for fluorometric measurement of protease enzyme activity, as reported by Leytus et al., Biochem. Journal 209: 299–307 (1983) and Leytus et al., Biochem. Journal 215: 253–260 (1983). The Leytus et al., substrates were extremely sensitive for measurement of enzyme activities, as compared to previously reported substrates. However, the Leytus et al. rhodamine 110 derivative substrates have been found to exhibit low water solubility of about 120 micromolar at 37° C., thereby necessitating the addition of organic solvent additives, e.g. dimethylformamide and ethanol, for promoting the substrate solubility. However, addition of organic solvents to enzyme assays is known to interfere with the assay procedure, i.e. denaturing the protein, decreasing reaction rate and/or causing precipitation of the other reactants or products, resulting in less than optimum test performance.

In addition to the disclosure of Leytus et al., a coumarin derivative substrate for the fluorometric and spectrophotometric determination of proteolytic enzymes in biological fluids was disclosed by Smith et al., U.S. Pat. No. 4,294,923. The Gargiulo et al. U.S. Pat. Nos. 4,275,153 and 4,336,186 disclose a fluorogenic aminoisophalate substrate for determination of protease enzyme activities in biological samples.

SUMMARY OF THE INVENTION

The present invention relates to water soluble xanthylium derivative substrates, hereinafter referred to as rhodamine 110 and rhodol water soluble derivative substrates, for fluorometric and spectrophotometric measurement of protease enzyme activities which, because of their water solubility at working concentrations, obviate the necessity of using organic solubilizing agents, e.g. dimethylformamide and ethanol, and thus eliminates their concomitant test interferences. In addition, the water soluble rhodamine 110 and rhodol derivative substrates exhibit greater sensitivity for determining levels of enzyme activities than the rhodamine 110 derivative substrates of the prior art. Consequently, as a result of this increased sensitivity, the water soluble rhodamine 110 and rhodol derivative substrates have utility in spectrophotometric test procedures; whereas, the prior art rhodamine 110 derivative substrates of low water solubility do not exhibit the sensitivity sufficient to be used with smaller volumes of sample and substrate to obtain both spectrophotometric and fluorescent determinations. The water soluble xanthylium derivative substrates of the present invention are useful to measure the activity of protease enzymes, cofactors, inhibitors, activators, and antiactivators, individually or in combination with each other, and specifically to measure the activity of trypsin-like enzymes.

An object of this invention is to provide a water soluble complex of xanthylium derivative substrates with side chains which are hydrolyzed by the enzymes, such that the hydrolysis of the side chains is directly proportional to the enzyme activity.

Another object of this invention relates to providing xanthylium derivative substrates with increased water solubility.

A further object of this invention, as compared to the prior art, is to eliminate the need for organic solvents in the assay procedures for measuring the activity of protease enzymes, cofactors, inhibitors, activators, and antiactivators, and specifically thrombin formation.

A still further object of this invention is to provide xanthylium derivative substrates with sufficient sensitivity to perform spectrophotometric, as well as fluorometric, measurements.

PREFERRED EMBODIMENTS

The synthetic substrates herein and their hydrolysis products are water soluble at working concentrations, thereby permitting their use for both spectrophotometric and fluorescent measurements, without the use of organic solvent additives and/or special water solubilizing agents. The novel water soluble substrates have the following general formulas:

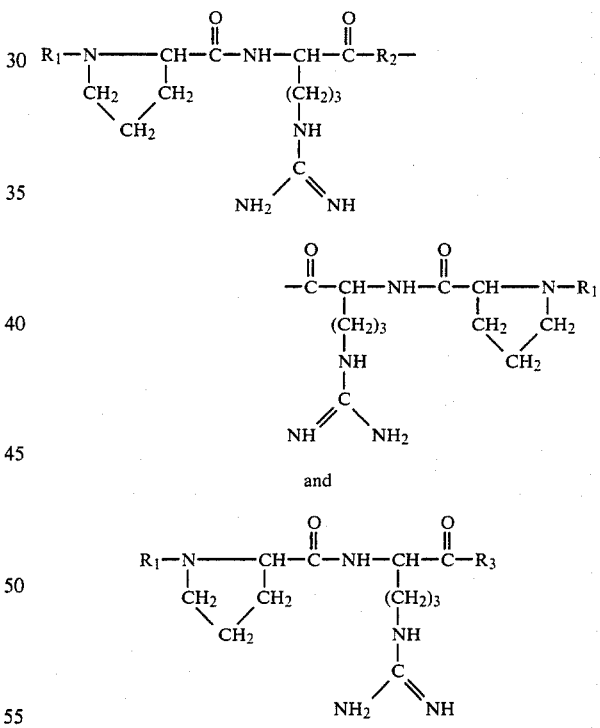

wherein:
- $R_1$ is a water solubilizing radical selected from the group consisting of sarcosyl, pyroglutamyl, and glutaryl;
- $R_2$ is xanthylium, 3', 6'-diamino-9'-(2-carboxyphenyl); and
- $R_3$ is xanthylium, 3'-amino-6'-hydroxy-9'-(2-carboxyphenyl) and the water soluble salts thereof.

The chemical structure for rhodamine 110 and rhodol are set forth below:

Rhodamine 110

-continued

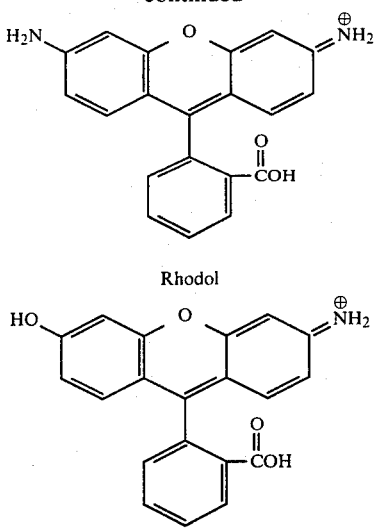

Rhodol

The sensitivity of the protease enzymes for these compounds is increased to include detection of lower levels of enzymes, inhibitor, cofactor, activator, and antiactivator than previously detectable using known methods; sensitivity being defined as the least detectable quantity. These improvements allow assay of thrombin by prothrombin time (PT), activated partial thromboplastin time (APTT) and thrombotest (TT) to be performed using the novel water soluble rhodamine 110 and rhodol derivative substrates of the present invention.

EXAMPLES

Synthesis of the water soluble xanthylium derivative substrates, analytic test results and examples of use of the substrates are described below. The following examples are not meant to limit the scope of the invention.

All amino acids used have the L - configuration, except as otherwise stated. The abbreviations used in the following examples are:

Arg = Arginine
Cbz = Carbobenzyloxy
DMF = Dimethylformamide
EDAC = 1-Ethyl-3-(3'-Dimethylaminopropyl)-Carbodiimide HCl
Glt = Glutaryl
HAc = Acetic acid
Pro = Proline
Pyro = Pyroglutamyl
Sar = Sarcosyl In the thin layer chromatography (TLC) analysis of the eluate and products, precoated glass plates are used with silica gel 60,254 (EM, Co. reagents) as absorption medium. For the development of the thin layer chromatograms, the following solvent systems are used:

$S_1$ = 2-butanone:acetone:$H_2O$; 8:1:1 (V/V)
$S_2$ = methanol:acetic acid:$H_2O$; 9:0.5:0.5 (V/V)

SYNTHESIS OF THE SYNTHETIC SUBSTRATES

Water soluble xanthylium derivative substrates are synthesized by first preparing a xanthene derivative substrate having the formula (H-L-Pro-Arg)$_2$-Rhodamine 110. The synthesis of (H-L-Pro-Arg)$_2$-Rhodamine 110, is fairly taught by Leytus et al.

EXAMPLE I

Prior Art

Step 1

Dissolve 0.96 g (2.62 mmol) of Rhodamine 110 in 400 mL of cold dimethylformamide (DMF) in a 1:1 ratio of volume to volume (V:V) with Pyridine at ice-bath temperature of 4° C., with concurrent stirring, and thereafter add to the admixture 25.6 g (135.5 mmol) of EDAC. After stirring for about one minute, rapidly add a solution of 11.52 g (33.41 mmol) of Cbz-L-Arginine-HCl in 96 mL of cold DMF:Pyridine solution in a 1:1 ratio. After a period of about 24 hours, the resulting product is isolated by adding 1.6 L of anhydrous ether, followed by centrifuging for about 10 minutes at 10,000 g, forming an oil-like product. The resulting oil is dissolved in 50 mL cold DMF and precipitated by the addition of 1.3 L cold acetone. The oil is separated by centrifugation for 10 minutes at 10,000 g. The oil is redissolved in 50 mL cold DMF and 500 mL cold 1.2 N HCl is added. A red precipitate is isolated by centrifugation for 10 minutes at 10,000 g. The red precipitate is dissolved in 50 mL cold methanol and precipitated by the addition of 350 mL cold ethyl acetate. The resulting precipitate, (Cbz-L-Arg)$_2$-Rhodamine 110, is collected by centrifugation for 10 minutes at 10,000 g. The last step is repeated three times.

Yield: 2.08g. (+79.4%) of (Cbz-L-Arg)$_2$-Rhodamine 110.

Step II

Dissolve 3.4 g (3.40 mmol) of (Cbz-L-Arg)$_2$-Rhodamine 110, as prepared in Step 1, in 75 mL of a 32% HBr-HAc solution. The resulting red colored solution is stirred at room temperature (RT) for about 1 hour. The resulting product is isolated by centrifugation with 800 mL of anhydrous ether. After repeating the centrifuging step an additional three times, the resulting brown solid, (H-L-Arg)$_2$-Rhodamine 110, is dried in vacuo for 16 hours.

Yield: 3.4 g (+100%) of (H-L-Arg)$_2$-Rhodamine 110.
TLC, S$_2$: R$_f$0.09.

Step III

Dissolve 2.75 g (2.79 mmol) of (H-L-Arg)$_2$-Rhodamine 110, as prepared in Step II, in 330 mL of a 1:1 DMF:Pyridine volume to volume (V:V) solution with concurrent stirring at ice-bath temperature of 4° C., and thereafter add an admixture of 32 g (166.9 mmol) of EDAC. After stirring for about one minute to accelerate dissolving, rapidly add a solution of 10.40 g (41.7 mmol) of Cbz-L-Proline in 60 mL 1:1 DMF:Pyridine solution. After a period of about 24 hours, the product is isolated by the procedures in Step 1. The resulting tan colored solid, (Cbz-L-Pro-Arg)2-Rhodamine 110, is dried in vacuo for 16 hours.

Yield: 1.86 g (52.0%) of (Cbz-L-Pro-Arg)$_2$-Rhodamine 110.
TLC, S$_2$: R$_f$0.44.

Step IV

Dissolve 1.80 g (1.40 mmol) of (Cbz-L-Pro-Arg)$_2$-Rhodamine 110, as prepared in Step III, in 45 mL of a 32% HBr-HAc solution, stirring the resulting red colored solution at room temperature (RT) for about 1 hour. The resulting product is isolated by centrifugation with anhydrous ether, as described in Step 1. The resulting brown colored solid, (H-L-Pro-Arg)$_2$-Rhodamine 110, is dried in vacuo for 16 hours.

Yield: 1.90 g (+100%) of (H-L-Pro-Arg)$_2$-Rhodamine 110.

TLC, S$_2$: R$_f$0.03.

EXAMPLE II

Procedure for Producing (H-Sar-Pro-Arg)$_2$-Rhodamine 110

Step A

Dissolve 1.90 g (1.63 mmol) of (H-L-Pro-Arg)$_2$-Rhodamine 110, as prepared in Steps 1–IV, in 190 mL of a 1:1 DMF:Pyridine solution at ice-bath temperature of 4° C., and thereafter add to the admixture 17.85 g (93.1 mmol) of EDAC. After stirring for about one minute to accelerate dissolving, rapidly add a solution of 5.20 g (23.3 mmol) of Cbz-Sarcosine in 40 mL of a 1:1 DMF:Pyridine solution. After a period of about 24 hours, the resulting product is isolated by the procedures described in Step 1. The resulting pink colored solid, (Cbz-Sar-Pro-Arg)$_2$-Rhodamine 110, is dried in vacuo for 24 hours.

The yield of (Cbz-Sar-Pro-Arg)$_2$-Rhodamine 110 is 1.1 g (49.6%).

Step B

Dissolve 1.1 g (0.78 mmol) of (Cbz-Sar-Pro-Arg)$_2$-Rhodamine 110, as prepared in Step A, in 24 mL of a 32% HBr-HAc solution, stirring the resulting deep-red solution at room temperature (RT) for about 1 hour. The resulting product is isolated by centrifugation with 350 mL of anhydrous ether. After repeating this step an additional three times, the resulting brown colored solid, (H-Sar-Pro-Arg)$_2$-Rhodamine 110, is dried in vacuo for 24 hours.

The yield of (H-Sar-Pro-Arg)$_2$-Rhodamine 110.5$\frac{1}{2}$ Hydrobromide Pentahydrate is 1.00 g (84.7%).

Elemental Analysis for C$_{48}$H$_{64}$N$_{14}$O$_{9}$5$\frac{1}{2}$ HBr5H$_2$O.

| Theoretical, % | Found, % |
|---|---|
| C = 38.00 | 37.84, 38.11 |
| H = 5.24 | 5.17, 4.81 |
| N = 12.93 | 12.69, 12.76 |
| Br = 29.03 | 29.58 |

TLC, S$_2$: Rf 0.01.

EXAMPLE III

Procedure for Producing (H-L-Pyro-Pro-Arg)$_2$-Rhodamine 110

Step A

Dissolve 380 mg (0.325 mmol) of (H-L-Pro-Arg)$_2$-Rhodamine 110, as prepared in Steps 1–IV, in 50 mL of a 1:1 DMF:Pyridine solution at ice-bath temperature of 4° C., and thereafter add to the admixture 3.58 g (18.62 mmol) of EDAC. After stirring for about one minute to accelerate dissolving, rapidly add a solution of 1.23 g (4.66 mmol) of Cbz-L-Pyroglutamic Acid in 11 mL of cold 1:1 DMF:Pyridine. After a period of about 24 hours, the resulting product is isolated by the procedures as described in Step I. The resulting brown colored solid, (Cbz-L-Pyro-Pro-Arg)$_2$-Rhodamine 110, is dried in vacuo for 16 hours.

The yield of (Cbz-L-Pyro-Pro-Arg)$_2$-Rhodamine 110 is 278 mg (57.1%).

Step B

Dissolve 78 mg (0.0521 mmol) of (Cbz-L-Pyro-Pro-Arg)$_2$-Rhodamine 110 in 3 mL of a 32% HBr-HAc solution and stir the resulting red colored solution at room temperature (RT) for about 1 hour. The resulting product is isolated by centrifugation with 75 mL of anhydrous ether. After repeating this centrifugation step three additional times, the resulting brown colored solid, (H-L-Pyro-Pro-Arg)$_2$-Rhodamine 110, is dried in vacuo for 16 hours.

The yield of (H-L-Pyro-Pro-Arg)$_2$-Rhodamine 110. 4$\frac{1}{2}$ Hydrobromide.5$\frac{1}{2}$ Hydrate is 57 mg (71.7%).

Elemental Analysis for C$_{52}$H$_{66}$N$_{14}$O$_{11}$4$\frac{1}{2}$ HBr5$\frac{1}{2}$ H$_2$O.

| Theoretical, % | Found, % |
|---|---|
| C = 40.90 | 40.54, 40.32 |
| H = 5.01 | 5.08, 5.06 |
| N = 12.85 | 12.55, 12.73 |
| Br = 23.60 | 23.56 |

EXAMPLE IV

Process for Producing (Glt-Pro-Arg)$_2$-Rhodamine 110

Step A

Dissolve 110 mg (0.094 mmol) of (H-L-Pro-Arg)$_2$-Rhodamine 110, as prepared in Steps 1–IV, in 12 mL of a 1:1 DMF:Pyridine solution at ice-bath temperature of 4° C., and thereafter add to the admixture 171 mg (1.5 mmol) of Glutaric anhydride. After a period of about 24 hours, the resulting product is isolated by the procedures as described in Step I. The resulting brown colored solid, (Glt-Pro-Arg)$_2$-Rhodamine 110, is dried in vacuo for 16 hours.

The yield of (Glt-Pro-Arg)$_2$-Rhodamine 110 is 118.3 mg (97.5%).

EXAMPLE V

Process for Producing Cbz-Arg Rhodol

Step A

Dissolve 3.5 g (0.54 mmol) of Rhodamine 110 in 25 mL of concentrated sulfuric acid at room temperature (RT) with concurrent stirring, and thereafter add to the admixture a solution of 700 mg (1.45 mmol) of sodium nitrite and 10 mL of concentrated sulfuric acid over a period of about 20 minutes. After a period of about 16 hours, the resulting admixture is poured into 250 g of ice-water. The resulting dark red solution, a diazo compound, is heated to a temperature of 65°–70° C. for about 30 minutes and nitrogen is evolved. The resulting lighter colored solution is filtered without cooling. After cooling, a red-brown flocculent precipitate is filtered, washed with a small amount of water and dried at 90° C. in vacuo for 16 hours. The red-brown flocculent product, Rhodol hemisulfate, appears to be 75% by TLC.

The yield of Rhodol hemisulfate is 3.5 g (96.6%).

TLC, S$_1$: R$_f$0.70.

Step B

Dissolve 1.14 g (3 mmol) of Rhodol hemisulfate in 500 mL of a 1:1 DMF:Pyridine solution at ice-bath temperature of 4° C., and thereafter add to the admixture a solution of 8.98 g (75 mmol) EDAC. After stirring for about one minute, rapidly add a solution of 6.55 g (19 mmol) of Cbz-L-Arg-HCl in 60 mL of a 1:1 DMF:Pyridine solution. After a period of about 24 hours, the resulting product was isolated by the procedures described in Step 1. The resulting reddish brown color solid, Cbz-L-Arg-Rhodol, is dried in vacuo for 16 hours.

The yield of Cbz-L-Arg-Rhodol is 0.2 g. (10%).

TLC, $S_1$: $R_f$ 0.20.

SOLUBILITY - COMPARISON OF (Sar-Pro-Arg)$_2$-RHODAMINE 110 AND (Cbz-Pro-Arg)$_2$-RHODAMINE 110 OF THE PRIOR ART

An example of the enhanced sensitivity of the water soluble rhodamine 110 derivative substrates is demonstrated by the following data: Thrombin reaction rates were determined with the water soluble substrate, (Sar-Pro-Arg)$_2$-Rhodamine 110 and with the low water soluble substrate (Cbz-Pro-Arg)$_2$-Rhodamine 110 of the prior art. Identical test conditions were used including temperature 37° C., volume 1.0 ml., and buffer 0.10M Aces pH 7.0, with 0.05M KCl. Since sarcosyl (Sar) and carbobenzyloxy (Cbz) have similar molecular weights, both were tested at 100 ug/ml. The use of 15% ethanol was required to promote the solubility of the (Cbz-Pro-Arg)$_2$-Rhodamine 110. The solubility of the Cbz derivative substrate, even with the addition of 15% ethanol, was up to 120 micromolar at 37° C. In contrast, the solubility of (Sar-Pro-Arg)$_2$-Rhodamine 110 was up to 120 millimolar at 37° C., a thousand-fold increase in solubility.

| Change In Absorbance, 496 nm/Unit Thrombin/mL | | |
|---|---|---|
| Prior Art (Cbz-Pro-Arg)$_2$-Rhodamine 110 | Present Invention (Sar-Pro-Arg)$_2$-Rhodamine 110 | |
| 80 micromolar | 80 micromolar | 800 micromolar |
| 0.122 | 1.700 | 2.872 |

The above data, comparing the prior art substrate to the substrate of the present invention, demonstrates that the water soluble derivative substrate of the present invention is approximately fourteen times more sensitive than the low water solubility substrate of the prior art at the same molar concentration. The substrate of the present invention is as much as twenty-four times more sensitive at the higher concentration of the water soluble substrate than the prior art substrate.

ASSAYS USING THE WATER SOLUBLE XANTHYLIUM DERIVATIVE SUBSTRATES

The novel water soluble xanthylium derivative substrates permit determination of the activity of proteolytic enzymes, inhibitors, cofactors, activators, and antiactivators by spectrophotometric and fluorescent determinations. The novel water soluble xanthylium derivative substrates can be substituted for the natural substrate, fibrinogen, in blood coagulation tests based on the clotting of fibrin.

To more fully understand the invention, several assay examples are next presented.

ASSAY EXAMPLES

EXAMPLE I

Spectrophotometric Assay of Thrombin with (Pyro-Pro-Arg)$_2$-Rhodamine 110

Dose response curves were determined for three different concentrations of thrombin by measuring absorbance increases at 468 nm and 496 nm. Working thrombin dilutions were prepared as follows: Purified human alpha-thrombin, Dr. John Fenton, N.Y. State Dept. of Health, was diluted to 1.04 U/mL, 0.52 U/mL and 0.26 U/mL in 0.05 M HEPES, pH 8.0, with 0.25 M NaCl and maintained at 4° C. The substrate, (Pyro-Pro-Arg)$_2$-Rhodamine 110, was dissolved to 78 ug/mL in 0.20 M HEPES, pH 8.0, with 0.3 M KCl. Disposable acrylic cuvettes with 1 cm light path, Centaur Sciences, Inc. were used. A one mL aliquot of substrate was pipetted into a cuvette and warmed to 37° C. in a heating block. A one mL sample of a working thrombin dilution was added to the cuvette. After mixing the thrombin and substrate, absorbances at 468 nm and 496 nm were determined for 30 seconds with a Hewlett-Packard Model 8450A spectrophotometer. The increased absorbances over the timed intervals were:

| | Absorbance, 0-30 seconds | |
|---|---|---|
| Thrombin, U/mL | 468 nm | 496 nm |
| 0.26 | 0.0461 | 0.0462 |
| 0.52 | 0.0912 | 0.0860 |
| 1.04 | 0.1766 | 0.1671 |

A linear relationship exists between the thrombin concentrations and the measured absorbances at each wavelength:

| | 468 nm | 496 nm |
|---|---|---|
| Correlation Coefficient, r = | 0.9999 | 0.9996 |

The relationship between the measured absorbances at 468 nm and 496 nm was: Correlation Coefficient, r=0.9998 The above data establishes the ability of absorbance readings to be measured at either 468 nm or 496 nm.

EXAMPLE II

Fluorescent Coagulation Factor Assays with (Sar-Pro-Arg)$_2$-Rhodamine 110

Fluorescent assays for coagulation factors VIII and IX, based on the activated partial thromboplastin time (APTT) assay, were performed with the substrate (Sar-Pro-Arg)$_2$-Rhodamine 110. The synthetic substrate was used to detect thrombin generation, substituting for the natural substrate fibrinogen present in both human and animal plasmas. Standard calibration curves were constructed with normal plasma, Thromboscreen TM from Curtin Matheson Scientific, which was used to correct factor VIII and IX deficient plasmas, George King Biomedical. The APTT reagent contained purified soybean phospholipids and ellagic acid activator, Dade Diagnostics. A 125 ug/ml sample of substrate was dissolved in 0.10 M ACES, pH 7.0, with 0.05 M KCl and 5 mM CaCl$_2$. A Turner model 430 spectrofluorometer with a temperature controlled sample cell holder (37° C.) was used to make the kinetic fluorescent measurements. Excitation and emission wavelengths were set at 468 nm and 525 nm, respectively. Glass test tubes were used to perform the plasma activations and disposable acrylic cuvettes, Centaur Sciences, Inc., were used for the fluorescent measurements.

A 100 uL aliquot of 0.85% saline or normal plasma diluted in saline was added to a test tube followed by the sequential addition of 100 uL of factor deficient plasma and 100 uL of the APTT reagent. The test tube was incubated in a heating block at 37° C. for 2 minutes, at which time 100 uL of 25 mM CaCl$_2$ was added and the incubation was continued for an additional 30 seconds. The incubation mixture was transferred to a cuvette containing 2.0 mL of the substrate solution prewarmed to 37° C. and the fluorescent rate measured. Linear dose response curves were obtained for factors VIII and IX between 1% and 100% of normal:

| Plasma Dilution | Factor Level, % Normal | Relative Fluorescence* Factor VIII | Factor IX |
|---|---|---|---|
| — | <1 | 0.119 | 0.121 |
| 1:250 | 1 | 0.121 | 0.127 |
| 1:25 | 10 | 0.148 | 0.154 |
| 1:2.5 | 100 | 0.333 | 0.333 |

*The relative fluorescence of 0.85 ug quinine sulfate/mL 0.1 N $H_2SO_4$ was 1.0 under the same measurement conditions, except for excitation and emission wavelengths of 350 nm and 450 nm, respectively.

EXAMPLE III

Spectrophotometric Asssy of Plasminogen with (Sar-Pro-Arg)$_2$-Rhodamine 110

Streptokinase activated plasminogen was measured in plasma samples and the results were compared to a standard fluorescent assay procedure, Pochron, S. P. et al., Thrombosis Research 13, 733–739 (1978). Lyophilized normal citrated plasma from Hyland Diagnostics was used to prepare the assay standard calibration curves. Streptokinase, Calbiochem-Behring was reconstituted to 2,000 units/mL in 0.02 M HEPES, pH 7.5. (Sar-Pro-Arg)$_2$-Rhodamine 110 was dissolved in 0.10 M ACES, pH 7.0, with 0.05 M KCl, to 375 ug/mL. The assay was performed with 20 uL each plasma sample and 50 uL $H_2O$ added to a semi-micro disposable cuvette, 1 cm light path, Evergreen Scientific. After warming to 37° C. in a heating block, 500 uL of the Streptokinase solution was added with mixing and allowed to incubate at 37° C. for 2 minutes 48 seconds. The activation time of 2 minutes 48 seconds was used, since it is the fixed timing increment of a COULTER ® DACOS ® Chemistry system. Full plasminogen activation occurs in about 2 minutes, but longer activation times to 15 minutes also can be used. A 500 uL aliquot of the substrate solution at 37° C. was then added and, following mixing, the absorbance was determined for 3 minutes at 460 nm using a Model 8450A Hewlett-Packard spectrophotometer. The activity of the Streptokinase plasminogen was expressed as % normal by comparison to the control plasma results. The results of twelve plasma samples with values ranging from 40% to 140% normal compared well to the reference assay results. The correlation coefficient for the compared data was, r=0.990, and the least squares equation was calculated as y=0.956x +4.08.

EXAMPLE IV

Spectrophotometric Prothrombin Time with (Sar-Pro-Arg)$_2$-Rhodamine 110

The prothrombin time (PT) is used to monitor the extrinsic pathway of blood coagulation. This test is performed by the addition of thromboplastin to a plasma sample, resulting in the activation of clotting factor proteases, with the ultimate formation of a fibrin clot. The rate of clot formation is measured and is directly related to the extrinsic clotting factor activities in the plasma sample. The synthetic substrate (Sar-Pro-Arg)$_2$-Rhodamine 110 can be substituted in this test for the natural substrate fibrinogen. The final extrinsic pathway clotting factor, thrombin, is detected by the synthetic substrate.

The substrate was prepared in 0.05 M Aces buffer, pH 7.5, at 40 uM concentration. Thromboplastin was added to the buffered substrate, 0.05 mL per 1.0 mL substrate, and the mixture warmed to 37° C. Twenty-five uL of a plasma sample was placed in a semi-micro acrylic cuvette, 1 cm. light path, Evergreen Scientific. One half milliliter of the thromboplastin substrate mixture was added to the cuvette containing the plasma sample and the change in absorbance at 496 nm measured with a Model 8450A Hewlett-Packard spectrophotometer. Synthetic substrate test results for 56 patient samples, including some from patients receiving the anticoagulants heparin and/or coumadin, were compared to prothrombin time (PT) clotting values. Three commercial thromboplastin reagents were used: General Diagnostics, Ortho Diagnostics, and Dade Diagnostics. The patient sample clotting times ranged from 9.8 to 40.6 seconds as determined by a Coag-a-Mate ® 2001, photo-optical clot detection system, General Diagnostics. The synthetic substrate test results were inversely related to the clotting assay values, and the correlation coefficients for the compared data using the 3 thromboplastins were −0.944, −0.953 and −0.963.

EXAMPLE V

Spectrophotometric Antithrombin III-Heparin Cofactor Assay with (Sar-Pro-Arg)$_2$-Rhodamine 110

Antithrombin III was measured in plasma samples using the water soluble substrate, (Sar-Pro-Arg)$_2$-Rhodamine 110, and the reference fluorescent substrate assay procedure of Mitchell, G. A. et al., Thrombosis Research 12, 219–225 (1978) and the results were compared. Five uL of plasma and 50 uL of purified water were added to a semi-micro disposable polystyrene cuvette, 1 cm light path, Evergreen Scientific. After warming to 37° C., a one-half milliliter aliquot of a solution containing 5 units/mL of thrombin and 10 units/mL of heparin, in buffered saline was added to the cuvette. The mixture was incubated at 37° C. for 2 minutes 48 seconds. An activation time of 2 minutes 48 seconds was used since it is the fixed time increment of the COULTER DACOS system. Five hundred uL of the water soluble substrate, at a concentration of 375 ug/mL in 0.1 M ACES, pH 7.0, with 0.05 M KCl at 37° C. was added to the cuvette. The change in absorbance at 460 nm was determined for 20 seconds. The results for 26 plasma samples with Antithrombin III levels ranging from 40 to 115% of normal correlated well with the reference assay values. The correlation coefficient for the compared data was, r=0.983 and the least squares equation was calculated as y=1.026x −2.90.

The novel water soluble xanthylium derivative substrate also can be used to simulanteously monitor the extrinsic and intrinsic pathways of thrombin formation by the well known thrombotest, a method first described by Dr. P. A. Owren, Lancet II, pp. 754–758 (1959). The thrombotest is sensitive to the factors of both the extrinsic and intrinsic pathways, and the thrombin generated from two pathways is approximately equal. The thrombotest reagents include thromboplastin, partial thromboplastin, adsorbed plasma, and fibrinogen. The novel water soluble xanthylium derivative substrates can be substituted in the thrombotest for the natural substrate, fibrinogen, to determine the activity of the thrombin formed.

The above examples support the use of the water soluble rhodamine 110 and rhodol derivative substrates in the universal coagulation tests, the prothrombin time, the activated partial thromboplastin and the thrombotest.

Although particular embodiments and examples of the invention have been shown and described in full here, there is no intention to thereby limit the invention to the details of such embodiments and examples. On the contrary, the intention is to cover all modifications, alternatives, embodiments, usages and equivalents of the subject invention as fall within the spirit and scope of the invention, specification and the appended claims.

What is claimed is:

1. A xanthylium derivative substrate selected from the group consisting of:

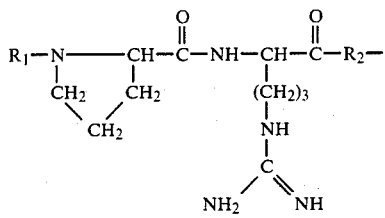

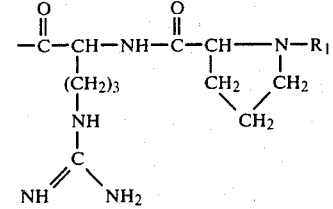

and

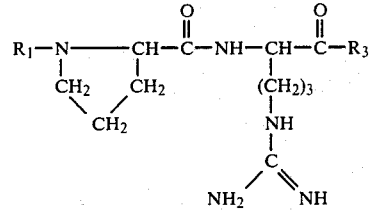

and acid salts thereof, wherein:
R$_1$ is a water solubilizing radical selected from the group consisting of sarcosyl, pyroglutamyl, and glutaryl;
R$_2$ is xanthylium, 3′, 6′-diamino-9′-(2-carboxyphenyl); and
R$_3$ is xanthylium, 3′-amino-6′-hydroxy-9′-(2-carboxyphenyl).

2. The substrate as defined in claim 1, wherein R$_1$ is sarcosyl.

3. The substrate as defined in claim 1, wherein R$_1$ is pyroglutamyl.

4. The substrate as defined in claim 1, wherein R$_1$ is glutaryl.